(12) United States Patent
Cazalas et al.

(10) Patent No.: US 10,709,403 B2
(45) Date of Patent: Jul. 14, 2020

(54) PROCESSING OF INTERVENTIONAL RADIOLOGY IMAGES BY ECG ANALYSIS

(71) Applicant: General Electric Company, Schenectady, NY (US)

(72) Inventors: Maxime Cazalas, Paris (FR); Regis Vaillant, Villebon sur Yvette (FR)

(73) Assignee: GENERAL ELECTRIC COMPANY, Schenectady, NY (US)

(*) Notice: Subject to any disclaimer, the term of this patent is extended or adjusted under 35 U.S.C. 154(b) by 859 days.

(21) Appl. No.: 13/748,794

(22) Filed: Jan. 24, 2013

(65) Prior Publication Data

US 2013/0190612 A1      Jul. 25, 2013

(30) Foreign Application Priority Data

Jan. 24, 2012   (FR) ...................................... 12 50693

(51) Int. Cl.
*A61B 6/00*           (2006.01)
*A61B 6/02*           (2006.01)
(Continued)

(52) U.S. Cl.
CPC .............. *A61B 6/5288* (2013.01); *A61B 6/02* (2013.01); *A61B 6/4208* (2013.01); *A61B 6/461* (2013.01);
(Continued)

(58) Field of Classification Search
CPC ..... A61B 19/5244; A61B 6/02; A61B 6/4208; A61B 6/461; A61B 6/485; A61B 6/486;
(Continued)

(56) References Cited

U.S. PATENT DOCUMENTS 4,274,422 A * 6/1981 Anderson ............ A61B 5/0456
                                                      600/440
5,188,116 A    2/1993 Pammrehn et al.
(Continued)

FOREIGN PATENT DOCUMENTS

CN        101073502 A      11/2007
CN        101111193 A       1/2008
(Continued)

OTHER PUBLICATIONS

Manka et al., "Performance of Simultaneous Cardiac-Respiratory Self-Gated Three-Dimensional MR Imaging of the Heart", Jun. 2010, radiology.rsna.org, Radiology: vol. 255: No. 3, pp. 909-916.*
(Continued)

*Primary Examiner* — Aaron B Fairchild
(74) *Attorney, Agent, or Firm* — Fletcher Yoder, P.C.

(57) ABSTRACT

A method of processing images for interventional imaging, wherein a region of interest is visualized, is provided. The method comprises acquiring a series of 2D images of the region of interest in a patient during at least one respiratory phase, acquiring an electrocardiographic signal which is synchronized with the acquisition of the series of 2D images, processing the electrocardiographic signal to estimate at least one deformation phase of the region of interest induced by the patient's respiratory movement, and registering the different successive 2D images in relation to the estimated deformation phase.

5 Claims, 4 Drawing Sheets

(51) Int. Cl.
*A61M 25/09* (2006.01)
*A61B 34/20* (2016.01)

(52) U.S. Cl.
CPC ............... *A61B 6/485* (2013.01); *A61B 6/54* (2013.01); *A61B 6/541* (2013.01); *A61M 25/09* (2013.01); *A61B 6/486* (2013.01); *A61B 6/504* (2013.01); *A61B 6/548* (2013.01); *A61B 34/20* (2016.02)

(58) Field of Classification Search
CPC ......... A61B 6/504; A61B 6/5288; A61B 6/54; A61B 6/541; A61B 6/548; A61B 6/5294; A61M 25/09
USPC ........................................................ 600/424
See application file for complete search history.

(56) References Cited

U.S. PATENT DOCUMENTS

| | | | |
|---|---|---|---|
| 6,256,368 B1* | 7/2001 | Hsieh et al. | 378/8 |
| 6,415,174 B1 | 7/2002 | Bebehani et al. | |
| 6,626,832 B1* | 9/2003 | Paltieli | A61B 8/0833 128/897 |
| 6,628,743 B1* | 9/2003 | Drummond et al. | 378/8 |
| 6,918,878 B2 | 7/2005 | Brodnick | |
| 7,426,256 B2* | 9/2008 | Rasche et al. | 378/8 |
| 7,729,743 B2 | 6/2010 | Sabczynski et al. | |
| 7,805,182 B2 | 9/2010 | Weese et al. | |
| 8,075,486 B2 | 12/2011 | Tal | |
| 8,300,765 B2 | 10/2012 | Gotman et al. | |
| 8,411,921 B2* | 4/2013 | Boese et al. | 382/131 |
| 2001/0031919 A1* | 10/2001 | Strommer et al. | 600/424 |
| 2002/0049375 A1* | 4/2002 | Strommer et al. | 600/407 |
| 2002/0172328 A1* | 11/2002 | Dekel | 378/205 |
| 2002/0181645 A1* | 12/2002 | Bruder et al. | 378/8 |
| 2003/0016782 A1* | 1/2003 | Kaufman et al. | 378/50 |
| 2005/0107688 A1 | 5/2005 | Strommer | |
| 2006/0287595 A1 | 12/2006 | Maschke et al. | |
| 2007/0027390 A1 | 2/2007 | Maschke et al. | |
| 2007/0093710 A1* | 4/2007 | Maschke | A61B 5/0066 600/407 |
| 2007/0100225 A1* | 5/2007 | Maschke | A61B 6/032 600/407 |
| 2007/0142715 A1* | 6/2007 | Banet | A61B 5/0006 600/301 |
| 2007/0167700 A1* | 7/2007 | Rahn et al. | 600/407 |
| 2008/0058917 A1* | 3/2008 | Klingenbeck-Regn | A61B 5/0066 623/1.11 |
| 2008/0147086 A1 | 6/2008 | Pfister et al. | |
| 2008/0152205 A1* | 6/2008 | Vaillant et al. | 382/132 |
| 2008/0226149 A1* | 9/2008 | Wischmann et al. | 382/131 |
| 2008/0287803 A1* | 11/2008 | Li et al. | 600/466 |
| 2008/0300478 A1* | 12/2008 | Zuhars et al. | 600/407 |
| 2009/0180589 A1* | 7/2009 | Wang et al. | 378/65 |
| 2009/0182224 A1* | 7/2009 | Shmarak | A61B 5/1107 600/424 |
| 2009/0208079 A1* | 8/2009 | Vaillant et al. | 382/131 |
| 2009/0245457 A1* | 10/2009 | Takeuchi et al. | 378/8 |
| 2009/0292309 A1 | 11/2009 | Maschke et al. | |
| 2010/0189217 A1* | 7/2010 | Abe | 378/62 |
| 2011/0069063 A1* | 3/2011 | Liao et al. | 345/419 |
| 2011/0201915 A1 | 8/2011 | Gogin et al. | |

FOREIGN PATENT DOCUMENTS

| | | |
|---|---|---|
| CN | 101190149 A | 6/2008 |
| CN | 102112055 A | 6/2011 |
| CN | 102196768 A | 9/2011 |

OTHER PUBLICATIONS

French Search Report dated Sep. 12, 2012 which has been issued in connection with French Patent Application No. 1250693 which was filed on Jan. 24, 2012.

Office Action issued in connection with corresponding CN Application No. 201310026154.3 dated Aug. 9, 2016.

* cited by examiner

PROCESSING OF INTERVENTIONAL RADIOLOGY IMAGES BY ECG ANALYSIS

BACKGROUND OF THE INVENTION

Embodiments of the invention concern the field of medical imaging, and in particular, the processing of images in interventional radiology (fluoroscopic images). More specifically it concerns a method and a system with which it is possible in real time to display a region of interest in a patient, in two or three dimensions, in which a surgical instrument can be inserted. Interventional radiology consists of a practitioner guiding and deploying one or more surgical instruments inside a patient's vascular system with the assistance of a medical imaging system.

The medical imaging system allows the acquisition, processing and real-time display of two-dimensional images (2D) showing the patient's vascular system and the surgical instrument(s). These images enable the practitioner to guide the instrument within the vascular system.

The acquisition of these images requires emitting of a low X-ray dose. The vessels are visible therein by means of a contrast agent previously injected into the patient's vascular system. However, it is not possible, for physiological reasons, to continually inject a contrast agent into a patient.

In addition, situations arise in which data can be obtained using specific imaging systems. In order to utilize the data sets derived from different sources the different images need to be placed within the same reference frame.

In addition, it may be useful to visualize the surgical instruments in relation to the patient's anatomy.

However, any alignment defect with two superimposed images is detrimental. For example, the practitioner may see the instrument at a position relative to the model that is different from its effective position in relation to the anatomy, which is detrimental to the necessary precision of the practitioner's intervention.

Alignment defects may result from the patient's physiological movements: for example heart beats and breathing. These movements may make guiding of the instrument more complex since the practitioner only has access to real time images in which the instrument may be shown at an inaccurate point relative to the data provided by the mask.

There is therefore a need to take into account the patient's physiological movements to improve firstly the duration, and secondly, the quality of the procedure.

BRIEF DESCRIPTION OF THE INVENTION

With the invention, it is possible in real time to characterize and to offset a patient's physiological movement during interventional procedure.

According to an embodiment of the invention, a method of processing images for interventional imaging, wherein a region of interest is visualized, is provided. The method comprises acquiring a series of 2D images of the region of interest in a patient during at least one respiratory phase, acquiring an electrocardiographic signal which is synchronized with the acquisition of the series of 2D images, processing the electrocardiographic signal to estimate at least one deformation phase of the region of interest induced by the patient's respiratory movement, and registering the different successive 2D images in relation to the estimated deformation phase.

According to an embodiment of the invention, a medical imaging system is provided. The medical imaging system comprises an acquisition unit configured to acquire a series of 2D images of a region of interest in a patient during at least one respiratory phase, and to acquire an electrocardiographic signal which is synchronized with the acquisition of the 2D images, and a computing unit configured to process the electrocardiographic signal to estimate at least one deformation phase of the region of interest induced by the patient's respiratory movement, and to register the different successive 2D images in relation to the estimated deformation phase.

BRIEF DESCRIPTION OF THE DRAWINGS

Other characteristics, objectives and advantages of the invention will become apparent from the following solely illustrative and non-limiting description, to be read with reference to the appended drawings in which.

DETAILED DESCRIPTION OF THE INVENTION

In all the figures, similar parts carry identical reference numbers.

In the course of an interventional radiology procedure, a practitioner may move one or more surgical instruments towards a region of interest in a patient by way of the patient's vascular system. The surgical instrument may be a catheter, whether or not equipped with electrodes, a guide wire, or any other instrument known to a person skilled in the art.

To facilitate moving of the instrument, a medical imaging system allows for the display of the region of interest (region to be treated) in real time. By means of this image, the practitioner may optionally visualize the position of the surgical instrument. The image is a mask of the region of interest which is acquired before the actual procedure. This mask may be a 2D image in which clinical relevant data has been acquired through the injection of a contrast agent, or using any other method known to a person skilled in the art.

It may also be a succession of 2D images acquired at different phases of the cardiac cycle, or a 3D image reconstructed from the acquired 2D images. A method of processing images which is described below allows the merging of the data sets derived from real-time images with the mask of the region of interest.

Therefore, the practitioner is provided with real-time information that may be utilized while performing the procedure.

Figure 1:
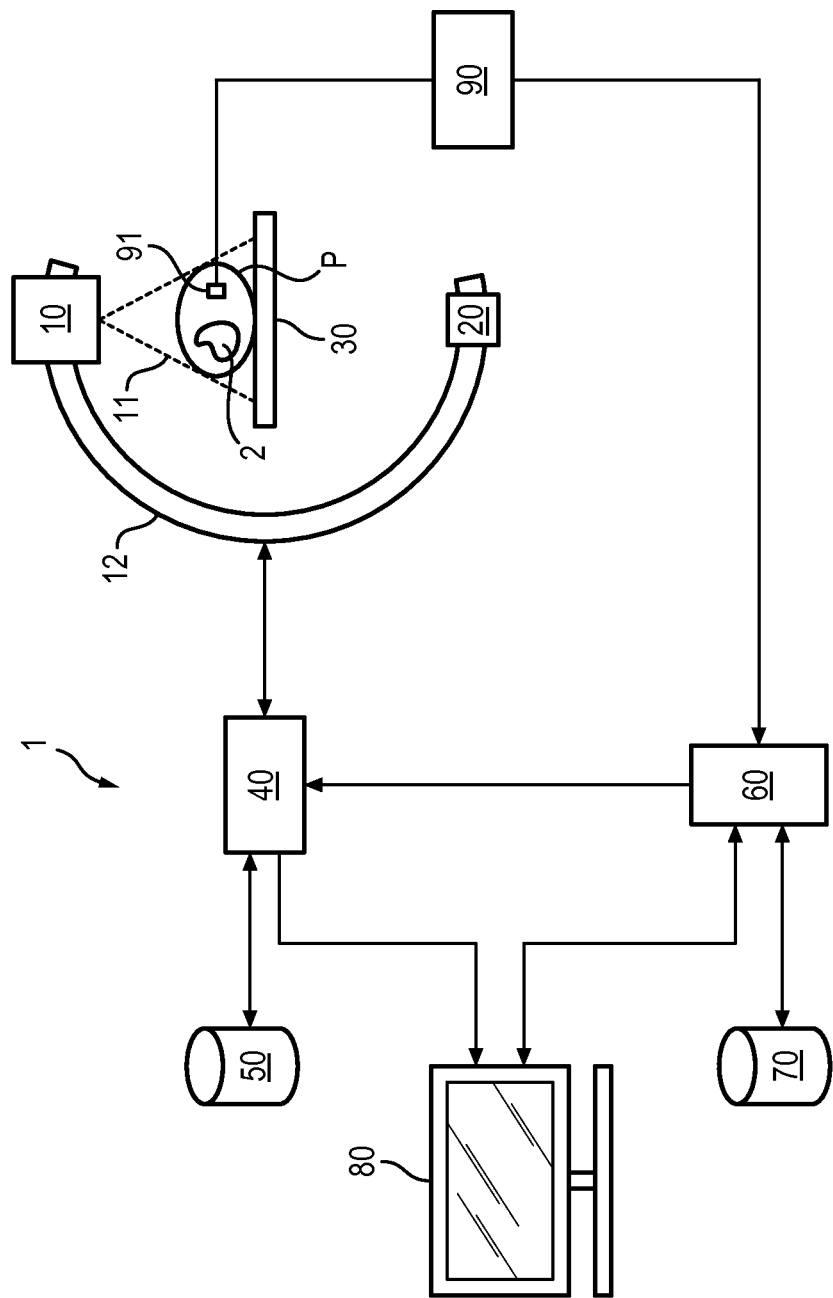
FIG. 1 illustrates a medical imaging system according to an embodiment of the invention.

FIG. 1 illustrates a medical imaging system 1 configured to acquire a mask of the region 2 to be treated in a patient P and a succession of 2D images of the region 2 of the patient to be treated during the interventional procedure.

The imaging system comprises an X-ray source 10 adapted to emit an X-ray beam 11, a detector 20 arranged opposite the X-ray source 10 and configured to detect the X-rays emitted by the X-ray source 10, a support 30 arranged between the X-ray source 10 and the detector 20, a control unit 40, a storage unit 50, a computing unit 60 connected to a storage unit 70, and a display unit 80.

In addition, the imaging system comprises an acquisition unit 90 configured to acquire an electrocardiographic signal of the patient, and a detection device 91 configured to detect this signal being emitted from the patient P.

The X-ray source 10 and the detector 20 are connected through a C-arm 12. The arm 12 as is known as a vascular access C-arm. The C-arm 12 can be oriented over three degrees of freedom.

The detector 20 may be a semiconductor image sensor comprising caesium iodide phosphor for example (scintillator) on a transistor/photodiode array in amorphous silicon. Other suitable detectors are: a CCD sensor, or a direct digital detector, which directly converts X-rays to digital signals. The detector 20 illustrated in FIG. 1 is planar and defines a planar image surface. Other geometries are also suitable.

The control unit 40 is connected to the C-arm 12 through a wire or wireless connection. The control unit 40 is used to control acquisition by setting several parameters such as the radiation dose to be emitted by the X-ray source, and the angular positioning of the C-arm 12. The control unit 40 can control the positioning of the C-arm 12, for example, the position of the source 10 relative to the detector 20. The control unit 40 may comprise a reader device (not shown), for example, a diskette reader, CD-ROM reader or connection ports to read the instructions of a processing method from an instruction medium (not shown), for example, a diskette, CD-ROM, DVD-ROM, or USB flash drive, or more generally, from any removable memory medium or by way of a network connection.

The storage unit 50 is connected to the control unit 40 to record the parameters and acquired images. It is possible to locate the storage unit 50 inside or outside the control unit 40. The storage unit 50 may be formed of a hard disk or SSD or any other removable, re-write storage medium (USB flash drives, memory cards etc.). The storage unit 50 may be a ROM/RAM memory of the control unit 40, a USB flash drive, a memory card, memory of a central server, or other suitable storage unit.

The display unit 80 is connected to the control unit 40 to display acquired images and/or data on the acquisition control parameters. The display unit 80 may be a computer screen for example or a monitor, flat screen, plasma screen or any other known type of display device. The display unit 80 enables the practitioner to control the acquisition of the radiological images.

A computing unit 60 is connected to a storage unit 70 and to the control unit 40. The computing unit 60 receives acquired images stored in the storage unit 50 and uses these images to perform a number of processing operations (see below).

The transmission of data from the storage unit 50 to the computing unit 60 can be made through an internal or external computer network or using any suitable physical memory medium, for example, diskettes, CD-ROM, DVD-ROM, external hard disk, USB flash drive, or SD card.

The computing unit 60 may be one or more computers for example, or one or more processors, one or more microcontrollers, one or more microcomputers, one or more programmable logic controllers, one or more application-specific integrated circuits, other programmable circuits, or other devices which include a computer such as a workstation.

As a variant, the computing unit 60 may comprise a reader device (not shown), for example, a diskette reader, CD-ROM or DVD-ROM reader, or connection ports to read the instructions of the processing method from an instruction medium (not shown), for example, a diskette, CD-ROM, DVD-ROM, or USB flash drive or more generally any removable memory medium or through a network connection. The computing unit 60 may be connected to the display device 80 (such as in FIG. 1) or else to another display unit (not shown).

Figure 2:
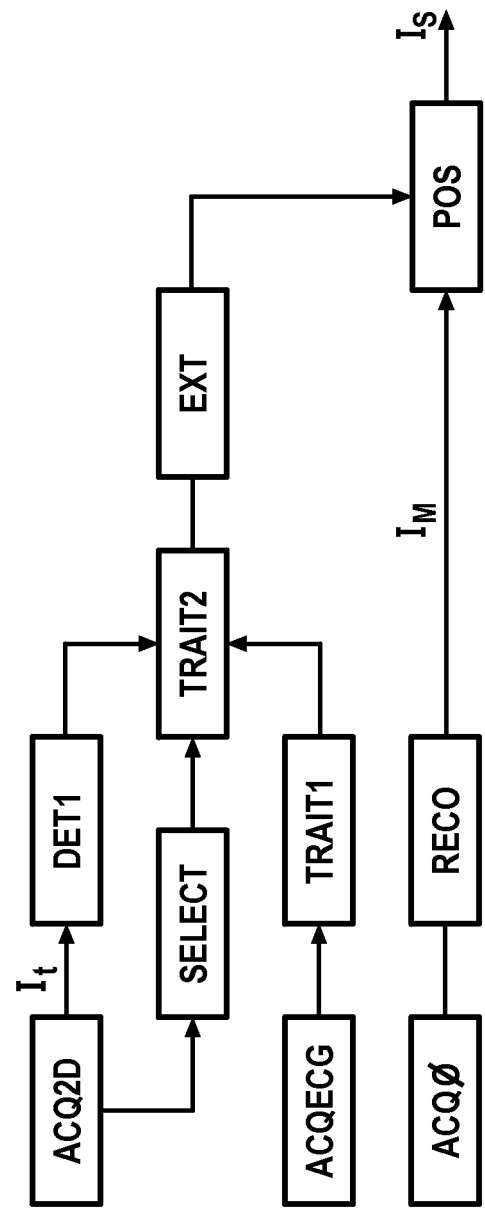
FIG. 2 illustrates steps of a method according to an embodiment of the invention.

FIG. 2 illustrates the steps of a method according to an embodiment of the invention.

At step ACQ0, a plurality of 2D images of the region of interest in the patient are acquired, the patient's respiratory movement being blocked. In this manner, it is possible to obtain several 2D masks of the region of interest, which will then be used solely with 2D images acquired within the same geometric configuration or a close geometric configuration.

Alternatively, it is possible from these acquired 2D images to implement the reconstruction, RECO, of a 3D image of the patient, thereby forming a 3D mask of the region of interest. For example, the region of interest may be the patient's heart region in which a stent is to be deployed, or in which a catheter equipped with electrodes is to be inserted.

Figure 3A:
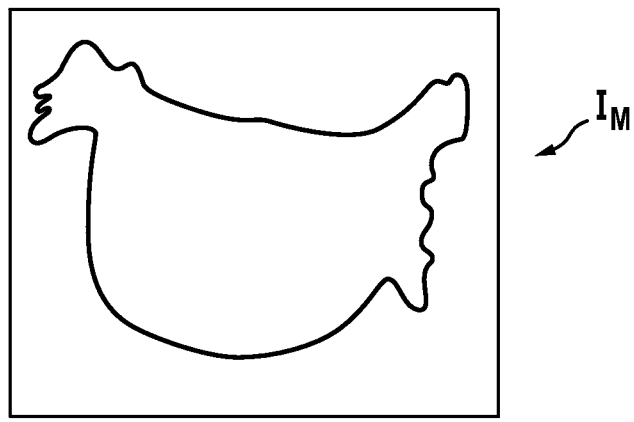
FIGS. 3a, 3b and 3c are images of the region of interest obtained with a method according to an embodiment of the invention.

In FIG. 3a, a mask $I_M$ of the region of interest is illustrated. After obtaining the mask $I_M$, the practitioner can insert the surgical instrument in the region of interest to carry out the procedure, if the instrument has not already been inserted.

During the procedure, at step ACQ2D, a succession of 2D images of the region of interest is acquired. The acquisition of these 2D images is conducted during at least one of the patient's respiratory phases. That is, a patient's inhalation and exhalation phase. In other words, the patient's region of interest here is subjected to a physiological movement, which is the patient's respiratory movement as well as cardiac movement.

Figure 3B:
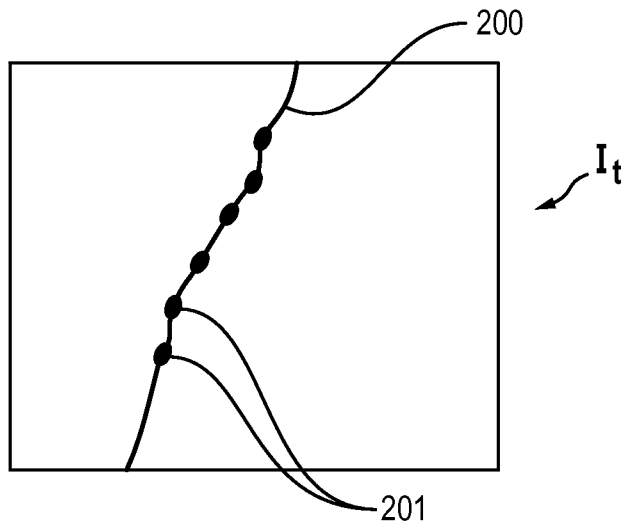
Figure 3C:
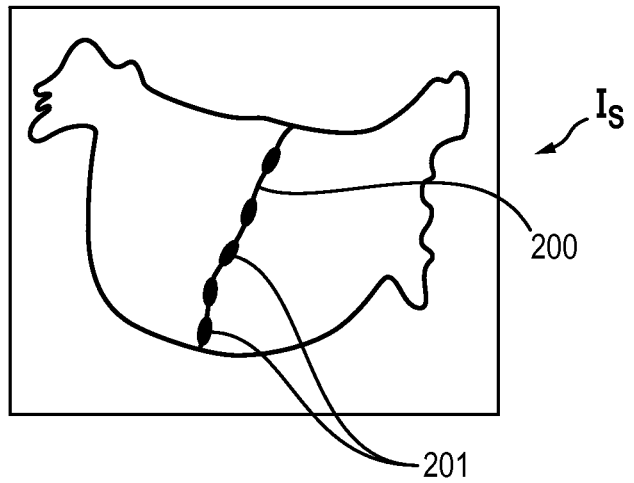

In FIG. 3b a 2D image $I_M$ of the region of interest is illustrated showing a catheter 200 equipped with electrodes 201 inserted in the region of interest of the patient. These images may be acquired at the same rate as the patient's heart rate to allow compensation thereof. For example, at step ACQECG, an electrocardiographic signal is acquired synchronously with the acquisition of the 2D images.

To complement the above, it is possible to perform a step DET1 during which the surgical tool is detected and tracked in each acquired 2D image. The step DET1 can be implemented using a mathematical morphological operation on the acquired 2D images by eliminating elements in the image, for example, all elements having a thickness greater than the diameter of the instrument. A size typically ranging from 6 to 9F (that is, a diameter of 2 to 3 mm) with electrodes with a length of 2 to 4 mm. Filtering can be performed to associate each pixel of the image to a certain probability of belonging to linear segments having a certain orientation. Finally, with the probability mapping applied to the obtained image, the 2D image is obtained with the instrument.

It is therefore possible to correlate each acquired 2D image in which the instrument is visualized with the patient's electrocardiographic signal.

From the electrocardiographic signal, it will be possible to deduct the patient's respiratory movement.

To do so, at step TRAIT1, the electrocardiographic signal is processed to estimate at least one deformation of the region of interest induced by the patient's respiratory movement.

The processing TRAIT1 of the electrocardiographic signal consists of detecting an envelope of the electrocardiographic signal to derive the patient's respiratory movement therefrom.

Figure 4C:
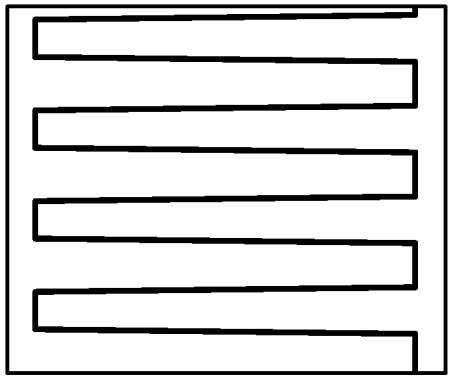
FIG. 4c illustrates an electrocardiographic signal obtained in a method according to an embodiment of the invention.
Figure 4B:
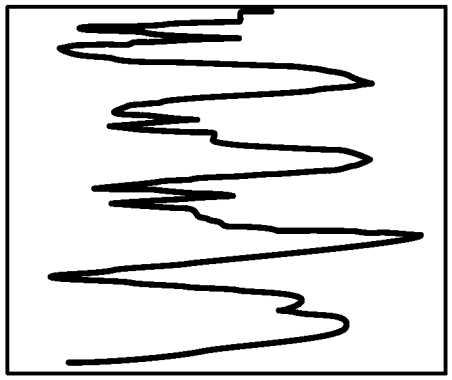
FIG. 4b illustrates an envelope of the electrocardiographic signal obtained in a method according to an embodiment of the invention.
Figure 4A:
FIG. 4a illustrates an electrocardiographic signal acquired in a method of an embodiment of the invention.

FIG. 4a illustrates the electrocardiographic signal S0 acquired during the procedure.

An electrocardiographic signal S1 is derived from the respiratory movement (see FIG. 4b) through the detection of the envelope of the electrocardiographic signal 100.

By filter processing the electrocardiographic signal derived from the respiratory movement 200 a signal S2 is obtained that represents the patient's movement. As illustrated in FIG. 4c, this signal is a succession of high and low states, the high state corresponding, for example, to an inhalation and the low state corresponding to an exhalation of the patient.

During this processing, the maxima of the signal S0 are extracted and the amplitude is calculated between two consecutive minima and maxima. In this manner the signal S1 is obtained. The signal S1 is then processed for smoothing by seeking the pseudo-periodic signal that best approximates the signal S2 over a defined time range. In this manner the signal S2 is obtained.

Therefore, the respiratory movement is determined by the signal S2, the amplitude of the associated deformation being either defined manually by the practitioner or computed automatically by matching points of interest detected in the images. In this latter case, there should be a strong correlation between the signal S2 and the automatically computed deformations. This property is then used to obtain more robust results from the automatic computing of deformations in pairs of images.

Finally, at step TRAIT2, the acquired 2D images are registered in relation to the estimated deformation.

For registration a reference is needed. For this purpose, at step SELECT, a 2D image is selected from among the series of successively acquired 2D images, with the selected 2D image forming a reference 2D image to estimate the deformation of the region of interest induced by the patient's respiratory movement. In particular, this reference 2D image corresponds to the patient's region of interest in the mask.

To complement the above, from the registered 2D images it is possible at step EXT to extract the position of the instrument in these registered 2D images.

Finally, at step POS, the registered 2D image is superimposed over a 2D or 3D mask of the region of interest to obtain an image in which the data set or sets derived from two types of acquisition are properly overlaid, the patient's respiratory movement having been offset.

According to an embodiment of the invention, the processing of the electrocardiographic signal consists of detecting an envelope of the electrocardiographic signal to deduce the patient's respiratory movement.

According to an embodiment of the invention, the 2D images are acquired at the rate of the patient's cardiac cycle.

According to an embodiment of the invention, a plurality of 2D images of the patient's region of interest are acquired, wherein the patient's respiratory movement being blocked, and utilizing each 2D image to form a mask of the patient's region of interest.

According to an embodiment of the invention, a 3D image of the patient is reconstructed from the 2D images of the patient's region of interest, and the reconstructed 3D image is utilized to form a 3D mask of the patient's region of interest.

According to an embodiment of the invention, a registered image is superimposed over the mask of the patient's region of interest.

According to an embodiment of the invention, a 2D image is selected from among the series of successively acquired 2D images, wherein the selected 2D image is utilized to form a reference 2D image for estimating the deformation phase of the region of interest induced by respiratory movement of the patient, the reference 2D image corresponding to the patient's region of interest in the 3D mask.

Embodiments of the invention make use of the electrocardiographic signal to obtain a signal representing the respiratory movement so as to offset movements of the region of interest caused by this movement.

In addition to an imaging system and method for processing images, embodiment of the invention provide a computer program product comprising program code instructions to implement the steps of the above-described method if it is run on a computer.

What is claimed is:

1. A method of processing images for interventional imaging, wherein a region of interest is visualized, the method comprising:
  acquiring a series of 2D X-ray images of the region of interest in a patient during at least one respiratory phase;
  acquiring a first electrocardiographic signal in synchronization with the acquisition of the series of 2D X-ray images so that the series of 2D X-ray images are acquired at the rate of patient's cardiac cycle;
  estimating, via a processor, from the electrocardiographic signal a period of deformation of the region of interest caused by respiratory motion of the patient; and
  registering, via the processor, different successive 2D X-ray images in relation to the estimated deformation period,
  wherein estimating the period of deformation from the electrocardiographic signal comprises detecting, via the processor, an envelope of the electrocardiographic signal to infer the respiratory motion of the patient therefrom.

2. The method according to claim 1, further comprising:
  acquiring a plurality of 2D X-ray images of the region of interest, wherein the patient's respiratory movement is blocked; and
  utilizing, via the processor, each of the plurality of 2D X-ray images to form a mask of the region of interest.

3. The method according to claim 2, further comprising:
  reconstructing, via the processor, a 3D image of the patient from the plurality of 2D X-ray images of the region of interest; and
  utilizing, via the processor, the reconstructed 3D image to form a 3D mask of the region of interest.

4. The method according to claim 3, further comprising superimposing, via the processor, a registered 2D X-ray image over the 3D mask of the region of interest.

5. A medical imaging system comprising:
  an acquisition unit configured to acquire a series of 2D X-ray images of a region of interest in a patient during at least one respiratory phase, and to acquire an electrocardiographic signal in synchronization with the acquisition of the series of 2D X-ray images so that the series of 2D X-ray images are acquired at the rate of the patient's cardiac cycle; and a computing unit configured to,
　　estimate from the electrocardiographic signal a deformation period of the region of interest caused by respiratory motion of the patient by detecting an envelope of the electrocardiographic signal to infer the respiratory motion of the patient therefrom; and
　　register different successive 2D X-ray images in relation to the estimated deformation period.

\* \* \* \* \*